(12) United States Patent
Swart et al.

(10) Patent No.: US 6,360,380 B1
(45) Date of Patent: Mar. 26, 2002

(54) OVERFLOWING SOAKER BATH TUB

(75) Inventors: Peter W. Swart, Oostburg; Ronald A. Bauer, Belgium; Carter J. Thomas, Cedarburg; Michael G. Cook, Kohler; Robert C. Giese; David J. O'Connell, both of Sheboygan, all of WI (US)

(73) Assignee: Kohler Co., Kohler, WI (US)

( * ) Notice: Subject to any disclaimer, the term of this patent is extended or adjusted under 35 U.S.C. 154(b) by 0 days.

(21) Appl. No.: 09/633,400

(22) Filed: Aug. 7, 2000

(51) Int. Cl.[7] ................................................. A47K 3/00
(52) U.S. Cl. ............................................. 4/541.1; 4/584
(58) Field of Search ............................... 4/541.1–541.5, 4/584, 591; 239/20

(56) References Cited

U.S. PATENT DOCUMENTS

| | | | |
|---|---|---|---|
| 1,781,325 A | 11/1930 | Dowling | |
| 2,529,568 A | 11/1950 | O'Hara | 4/173 |
| 3,967,323 A | 7/1976 | Serio | 4/173 R |
| 4,364,132 A | 12/1982 | Robinson | 4/546 |
| 4,371,995 A | 2/1983 | Donhauser | 4/538 |
| 4,535,489 A | 8/1985 | Elkins | 4/546 |
| 4,945,908 A | 8/1990 | Schneider | 128/369 |
| 5,580,621 A | 12/1996 | Kuszaj et al. | 428/34.1 |
| 5,720,056 A | 2/1998 | Aymes | 4/488 |
| 5,920,923 A | 7/1999 | Jillette | 4/541.1 |

*Primary Examiner*—Charles E. Phillips
(74) *Attorney, Agent, or Firm*—Quarles & Brady LLP

(57) ABSTRACT

Disclosed herein is a bath tub having a deep basin without an internal overflow. Instead, an overflow trough encircles the basin and collects water falling over a rim of the basin. A pump directs water within the overflow trough through a conduit back into the basin, so as to continuously maintain water flowing over the rim of the basin. Micro-effervescence and a chromatherapy system can also be provided with such a tub.

20 Claims, 9 Drawing Sheets

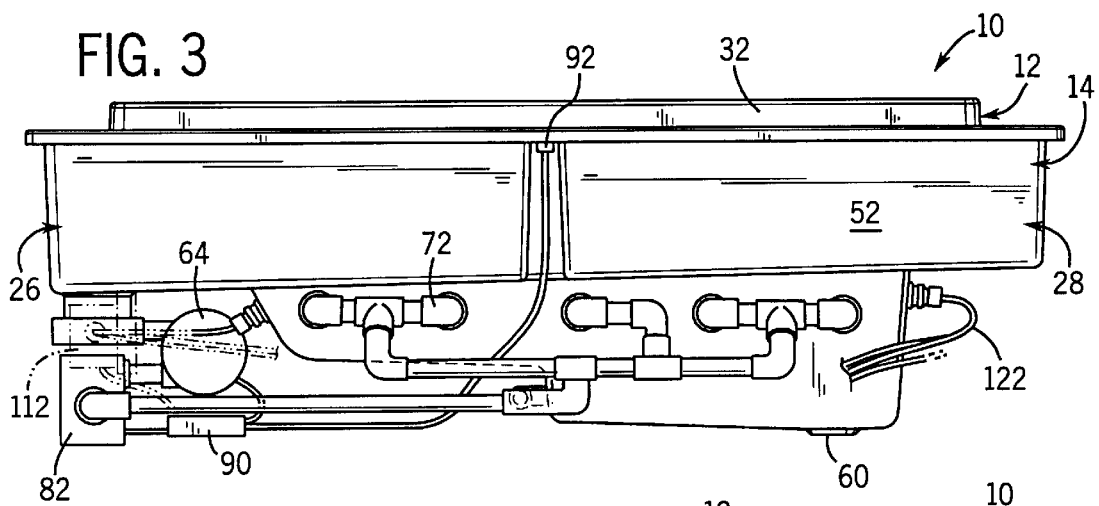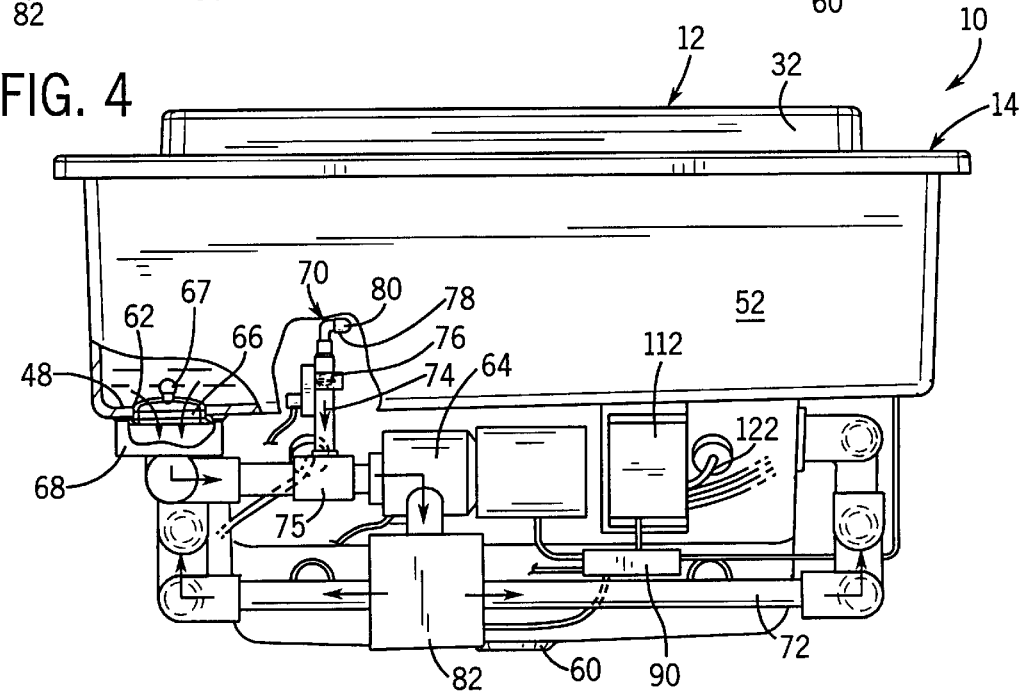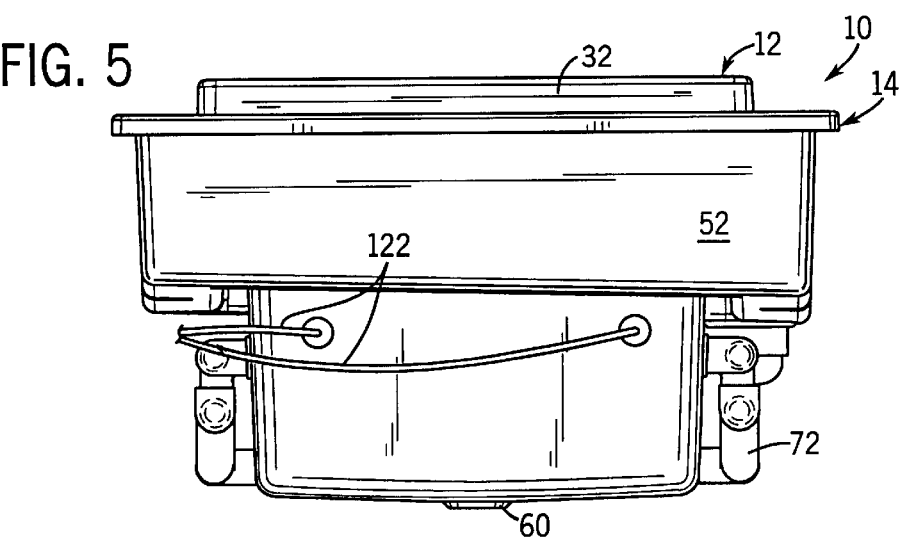

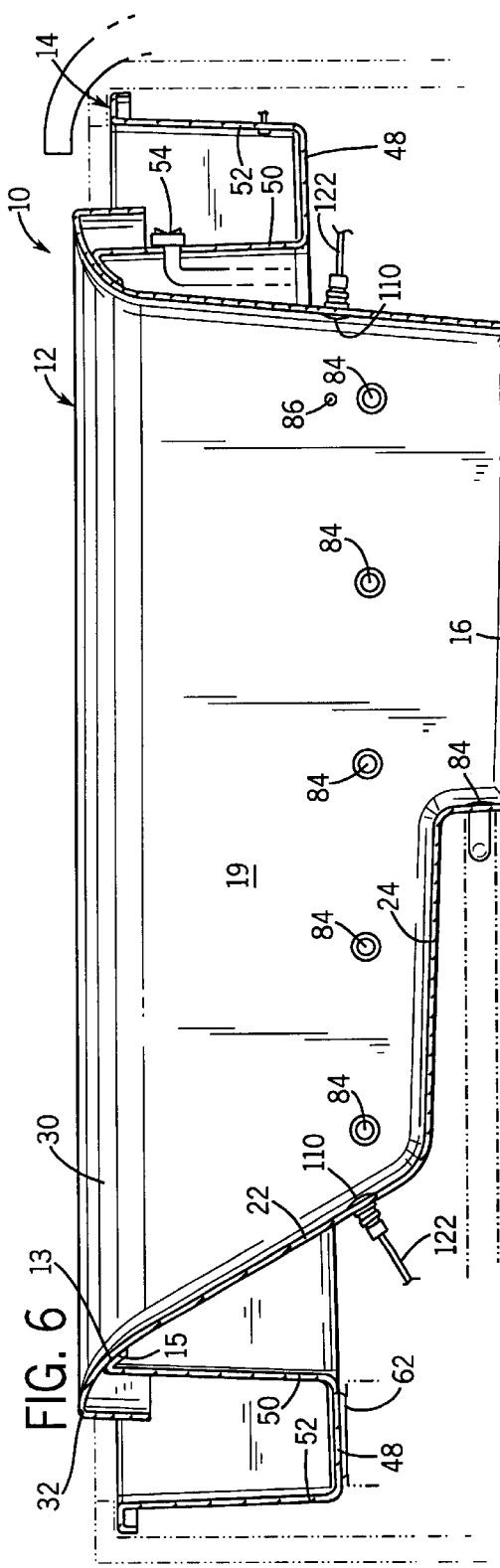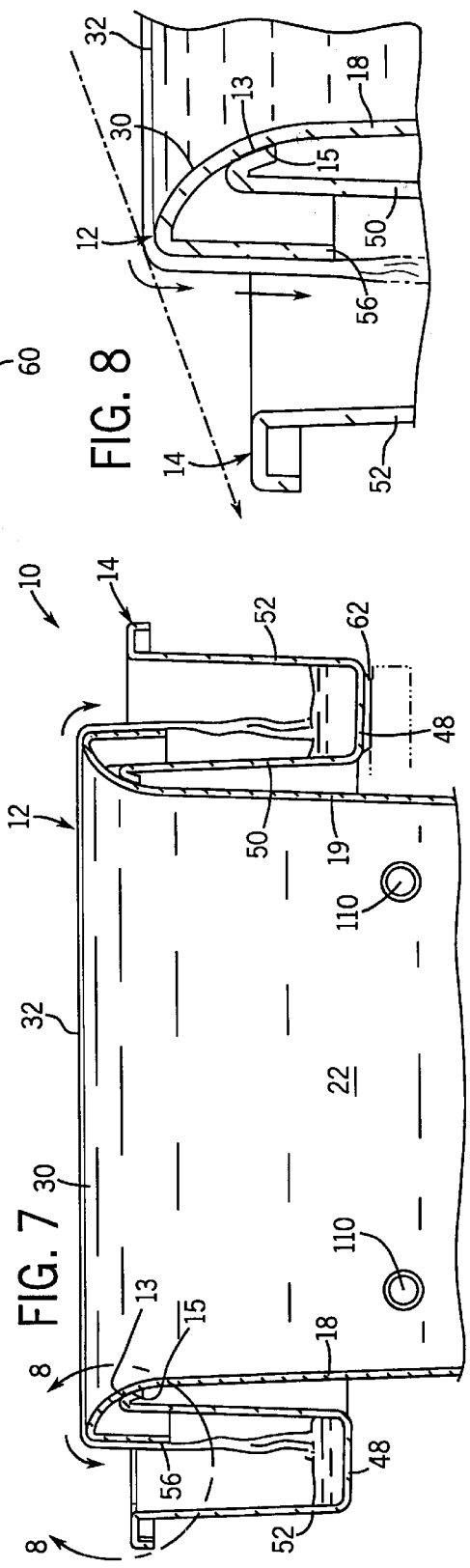

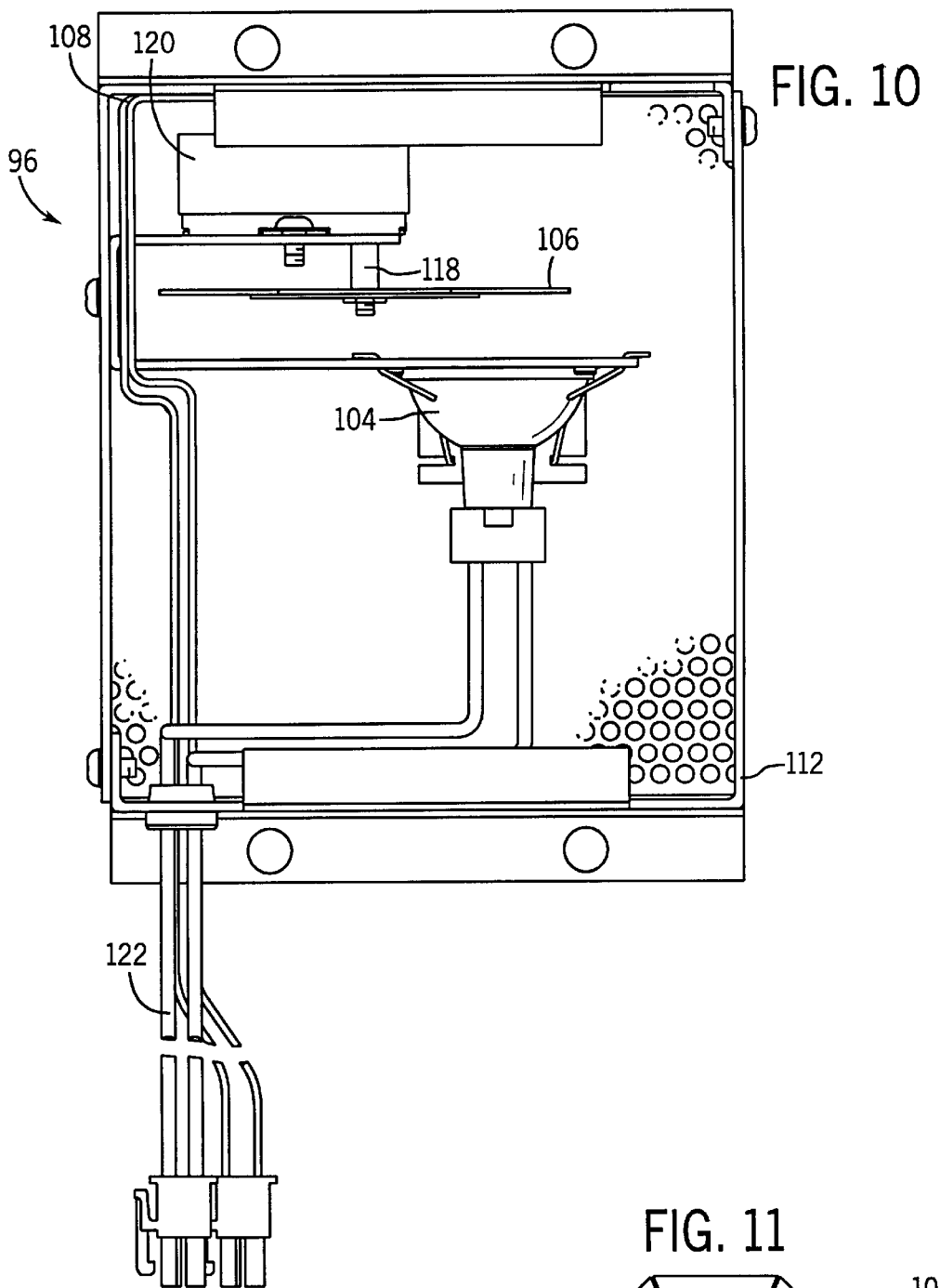

OVERFLOWING SOAKER BATH TUB

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to bath tubs, and in particular to soaker bath tubs, that use recirculated water to provide a deep basin of water and an aesthetically pleasing continuous overflow of water.

Basins of conventional bath tubs are typically shorter than average adults. An adult bather must therefore usually sit or lay within the basin with his or her knees bent and upper body leaning against the basin backrest. Conventional basins are typically so shallow that an adult bather's upper torso is entirely above the water when bathing. The bather can reposition so that his or her upper torso is submerged, but then portions of the bather's legs or side will be out of the water.

Soaker tubs have therefore been developed to allow a bather to submerse more of his or her body at one time during bathing. Such tubs can be similar in overall size and shape to conventional bath tubs, albeit with an extra deep basin. However, such tubs are still typically provided with an overflow outlet a few inches below the basin top. Even when using such tubs, for any given depth of basin, an unnecessary amount of the torso still projects out of the water during bathing.

Apart from soaking depth, there is also a desire to diversify the aesthetics of the bathing experience.

SUMMARY OF THE INVENTION

The present invention relates to bath tubs having a basin with a bottom wall and side walls extending to an upper rim. There is an overflow trough disposed radially outward around at least a majority (preferably 80%, 90% or even 100%) of a perimeter of the basin at one height for collecting water falling from the upper rim. There are also a conduit that provides fluid communication between the overflow trough and basin, and a pump associated with the conduit for delivering water from the trough to the basin via the conduit.

In preferred forms the upper rim of the basin is higher than an uppermost part of the overflow trough, and the bottom of the basin is formed with a seat area. There can also be adjustable leveling feet attached to an underside of the basin. Each leveling foot can have a mounting block attached to the underside of the basin and having a clearance opening therein. There can be a plate mounted to the mounting block and having a threaded bore there through in registration with the clearance opening of the mounting block. A heel can have a base from which extends a threaded rod sized to mate with the threaded bore so that the heel of the leveling foot can be moved vertically relative to the plate.

There can also be a drain control that operates a drain plug disposed in an opening in a bottom wall of the basin. The drain control is mounted to an inner side wall of the overflow trough, directly below a perimeter ledge of the basin (so as to be sheltered thereby). Preferably the pump can be operated at a speed below 2,000 revolutions per minute (so as to be extremely quiet).

There can also be a water level sensing system electrically coupled to the pump such that the pump will not operate if the water level within the basin is below a selected first level, or the water level in the overflow trough is below a selected second level. There can also be an aerator coupled to the conduit which can be selectively by-passed, the aerator being positioned at the suction side of the pump.

In yet another aspect the system can have a chromatherapy system for illuminating water within the basin with colored light. Preferably the chromatherapy system is polychromatic, has a spectral filter in the form of a rotatable color wheel, and will only illuminate the basin when the water within the basin couples a pair of basin sensors.

The present invention thus provides a more complete body soak for any given depth of basin (as no overflow protection is provided below the top of the basin), and that the system provides a continuous overflow of water from the basin while the bather is in the water. This provides a soothing and aesthetically pleasing effect.

Once the soaking tub has been initially filled to an operational level, no further water from a building supply is needed. Water collected by the surrounding overflow trough will be filtered, optionally heated, optionally aerated, and then recirculated back to the basin via a pump.

Important to the visual effect is the provision of adjustable leveling feet which insure an overflow over the complete 360 degrees of the upper basin rim. This helps hide the rim itself during operation. The bathing experience and visual perception is also enhanced by a chromatherapy system that can color the water within the basin with an array of soothing hues.

A water level sensing system (operated by touch-sensitive controls with lighted feedback indicators) prevents the pump from being operated at insufficient water levels and provides an auto-off feature for all electronic components.

The foregoing and other advantages of the invention will appear from the following description. In that description reference is made to the accompanying drawings which form a part hereof and in which there is shown by way of illustration preferred embodiments of the invention. These embodiments do not represent the full scope of the invention. Thus, the claims should be looked to in order to judge the full scope of the invention.

BRIEF DESCRIPTION OF THE DRAWINGS

FIG. 3 is a front elevational view thereof;

FIG. 4 is a partially fragmented and slightly enlarged left side elevational view of the head end of the tub;

FIG. 5 is a right side elevational view of the foot end of the tub;

FIG. 6 is a sectional view taken along line 6—6 of FIG. 2;

FIG. 7 is a sectional view taken along line 7—7 of FIG. 2;

FIG. 8 is an enlarged cross-sectional view taken along arc 8—8 of FIG. 7;

FIG. 10 is a top view of the chromatherapy device of FIG. 9;

FIG. 11 is a front view of a color wheel used in the chromatherapy device of FIG. 9;

DETAILED DESCRIPTION OF THE PREFERRED EMBODIMENTS

Figure 1:
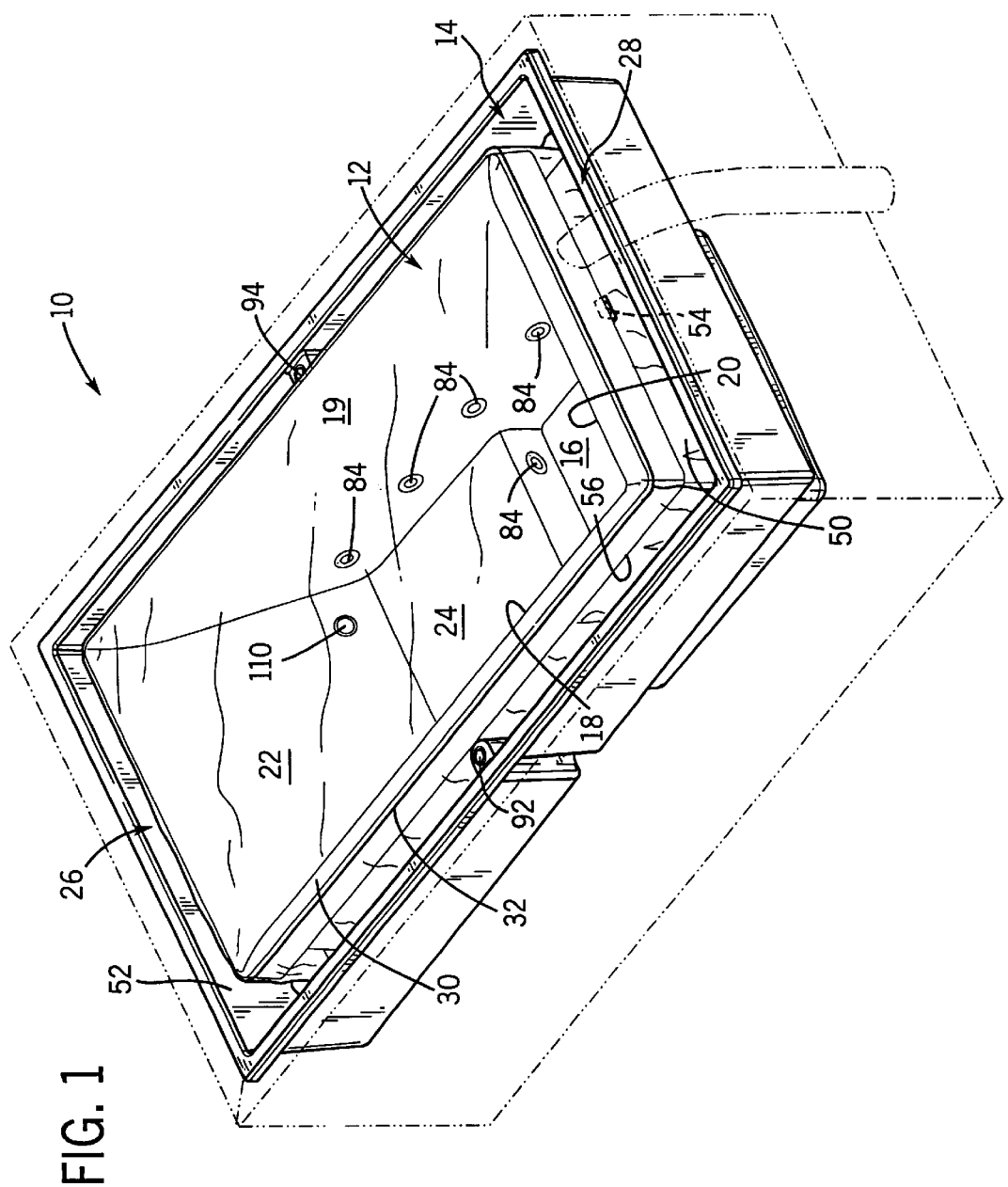
FIG. 1 is a top perspective view of a preferred bath tub of the present invention.

Referring first to FIG. 1, a tub 10 includes a generally rectangular basin 12 radially surrounded at its upper end by an overflow trough 14 for receiving water flowing over the basin 12. The tub 10 does not include an attached faucet and plumbing controls, but instead is positioned within a skirted mounting island (shown in hidden lines). As will be appreciated from FIG. 6, the tub is instead positioned somewhat near a water source (or a hose extending therefrom) so that when the tub is initially being filled the water will drop into the basin.

The basin 12 and overflow trough 14 can each be molded separately from a suitable material (such as fiberglass with a gel-coating applied to the top surfaces) to provide a smooth, high gloss finish on the inside of the basin 12 and overflow trough 14. The basin 12 and the overflow trough 14 can be joined together at the underneath side of the basin 12 by a high strength adhesive. Alternatively, the basin 12 and overflow trough 14 can be formed as a single piece.

As shown in FIGS. 6 and 8, a bonding surface 13 is preferably formed along the perimeter of the underside of the basin 12. The bonding surface is formed during the molding process by inverting the basin 12 and depressing a frame-like tool against the underside of the basin 12. The tool has a smooth slightly convex surface having the same contour and finish as a mating, gel-coated bonding surface 15 at the inside perimeter of the overflow trough 14.

The basin bonding surface 13 is smoother than the rest of the basin underside and follows the contour of the overflow trough convex bonding surface 15. The smooth bonding surfaces 13 and 15 provide suitable surfaces for establishing a sufficiently strong bond to adhere the overflow trough 14 to the basin 12.

Figure 2:
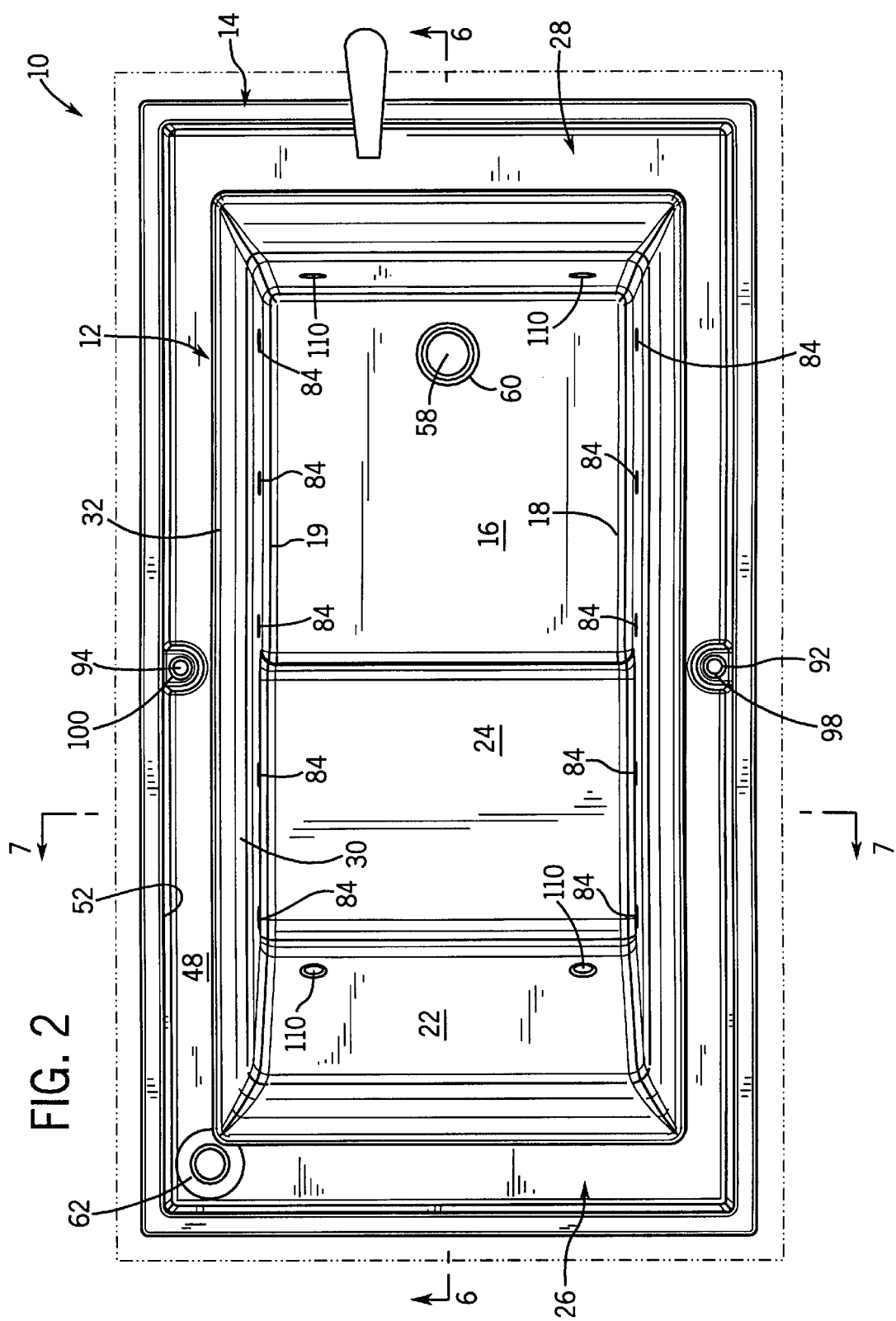
FIG. 2 is a top plan view thereof.
Figure 9:
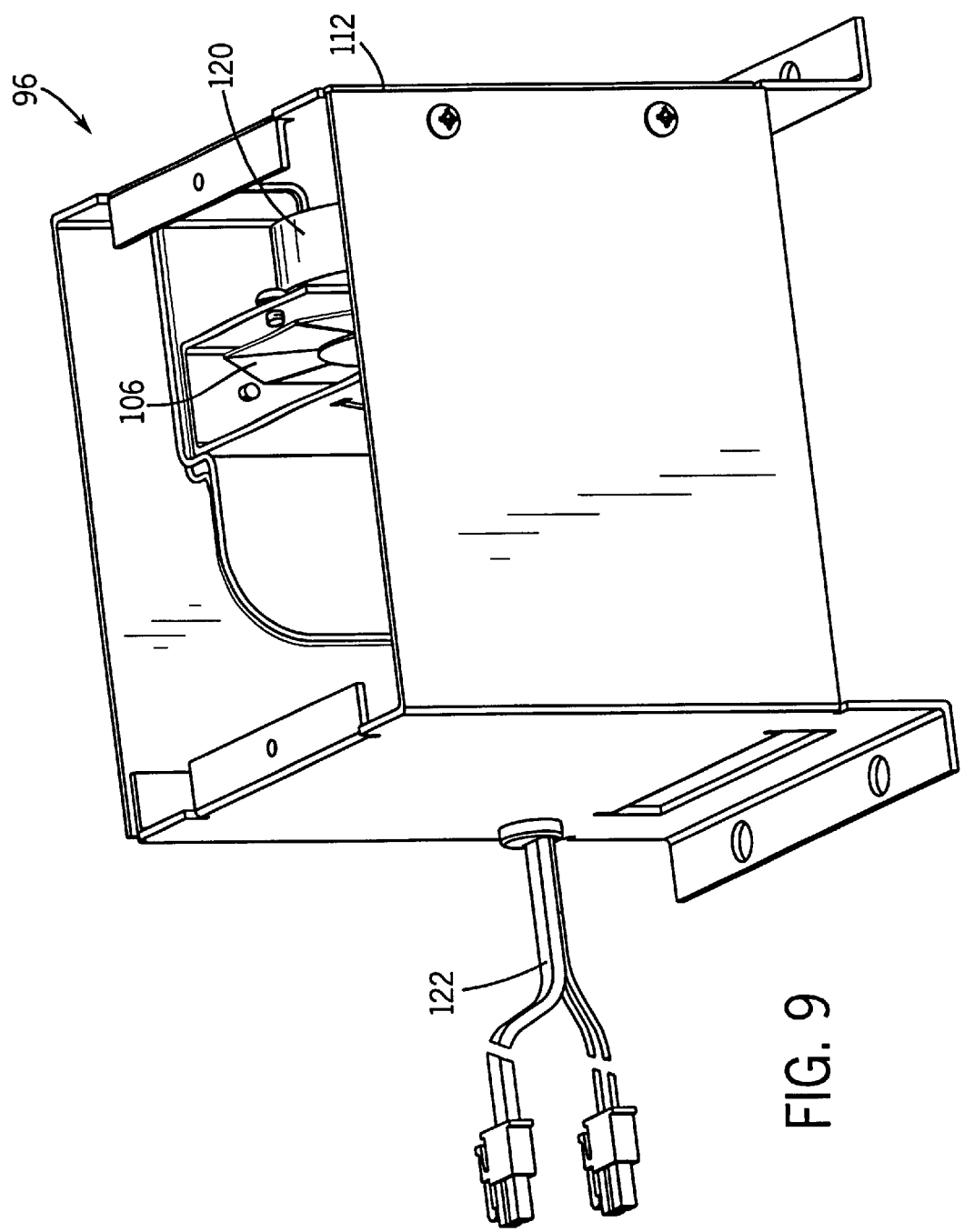
FIG. 9 is a perspective view of a fiber optic chromatherapy device useful in connection with the FIG. 1 tub.

Referring next to FIGS. 1, 2 and 6, the basin 12 has a bottom 16, generally upright side walls 18 and 19, a foot wall 20 and a backrest 22. The bottom 16 has a raised seat 24 which transitions into the backrest 22 to form a reclined seat. A bather can be seated with his or her head at a head end 26 and feet at a foot end 28, or with his or her head at the foot end 28 which allows for a second seating position at an increased depth.

The side walls 18 and 19, foot wall 20 and backrest 22 extend up from the bottom 16 sufficiently high so that an average adult bather seated therein can be submerged up to his or her neck. Thus, the soaker tub 10 is considerably deeper than conventional bath tubs. Preferably, the basin is 25" deep at the foot end 28 and 20" deep at the head end 26.

Note in particular that there is no overflow control in the basin wall. Thus, unlike a conventional bath tub where the water cannot rise above a few inches below the rim (because of the presence of an overflow opening), the entire depth of the tub can be filled with water.

Referring next to FIGS. 2, 6, 7 and 8, the top of the side walls 18 and 19, foot wall 20 and backrest 22 have a convex surface 30 that gradually slopes to a basin rim 32, which is the highest point of the tub 10. The rim 32 is preferably significantly higher than the overflow trough 14 so that the overflow trough 14 cannot be readily seen by a bather within the basin 12. This gives the bather the unique impression that water is overflowing freely without being contained.

The slope of the convex surface 30 eases water over the rim 32 and even allows a depth of water to blur or hide the side walls 18 and 19, foot wall 20 and backrest 22. These features give the basin 12 an essentially rimless effect. Additionally, the rim 32 is sufficiently narrow so that it can be grasped by a bather when entering and exiting the tub 10.

Figure 13:
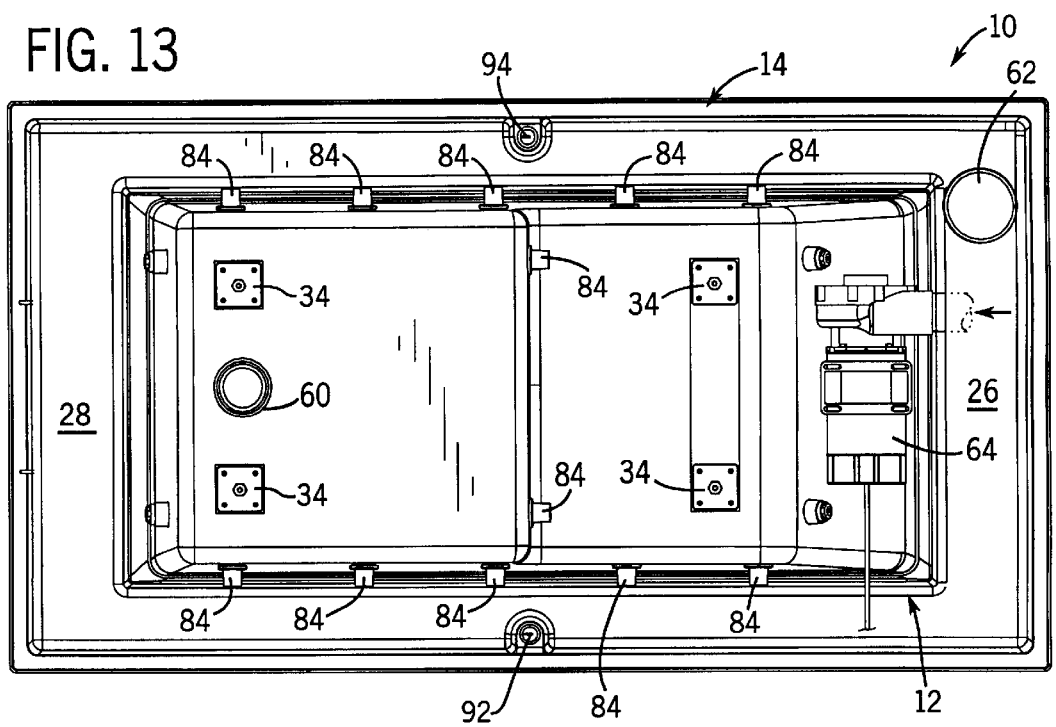
FIG. 13 is a schematic bottom view of the tub of FIG. 1, with focus on adjustable leveling feet.
Figure 15:
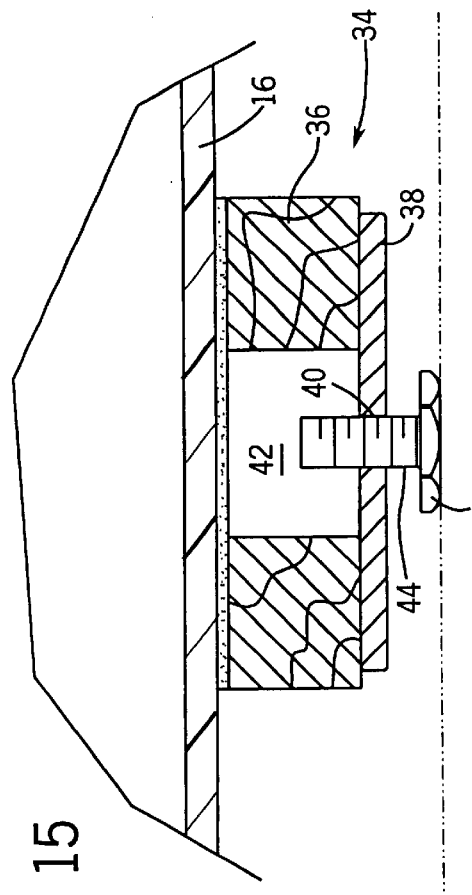
FIG. 15 is a sectional view taken along line 15—15 of FIG. 14.
Figure 14:
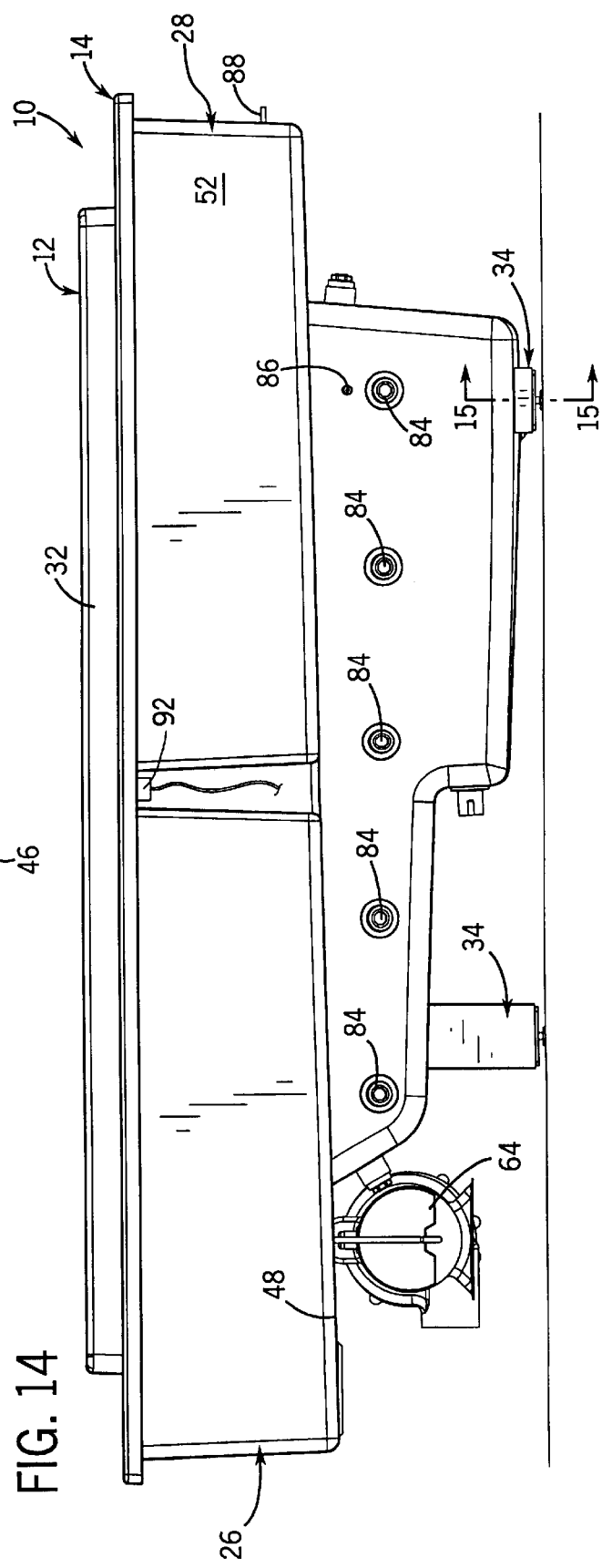
FIG. 14 is a view similar to FIG. 3, albeit further simplified for greater focus on the leveling feet.
Figure 16:
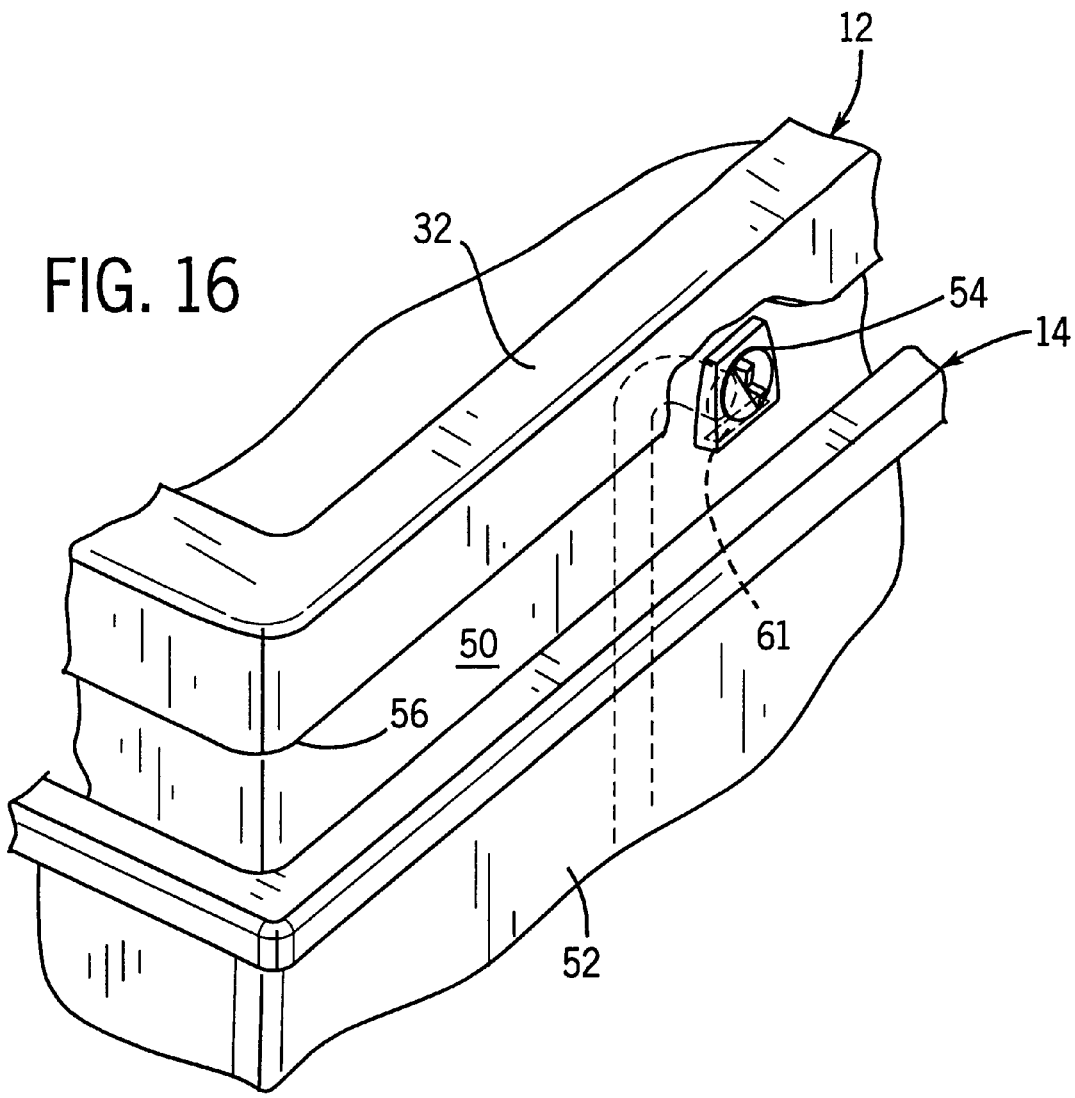
FIG. 16 is a detailed partial perspective view showing a drain control located in an overflow trough.

Referring next to FIGS. 13–15, the tub 10 can be leveled during installation by four adjustable feet 34 attached at the underside of the basin bottom 16. It is particularly desired that the tub 10 be accurately leveled so that water in the basin 12 runs uniformly over all parts of the rim 32. Water will then spill over the entire perimeter of the basin rim 32, ensuring the "rimless" effect is achieved and providing a level, glass-like surface.

As best seen in FIG. 15, the leveling feet 34 include a mounting block 36 attached to the underside of the basin bottom 16 by a fiberglass adhesive. Typically, two are at the foot end 28 and two are under the raised seat 24. The mounting blocks 36 at the raised seat 24 are taller than those at the foot end 28 to compensate for the differing in height of the bottom 16.

A mounting plate 38 is fastened to the bottom end of each mounting block 36. Each mounting plate 38 has a threaded bore 40 there through aligned with a through bore 42 in the corresponding mounting block 36. The threaded bore 40 engages a threaded shaft 44 of a heel 46 having a disk-shaped base. Each heel 46 can be rotated independently to advance or withdraw the heel 46 as needed to level the tub 10.

Referring again to FIGS. 1, 2 and 6, the basin 12 is encircled by the overflow trough 14. The overflow trough 14 forms a generally rectangular channel having a bottom 48 and opposite inner 50 and outer 52 side walls. A drain control 54 is mounted to the inner side wall 50 at the foot end 28. The drain control 54 is sheltered beneath a lip 56 of the basin 12 so as not to be in the path of water spilling over the rim 32. The drain control 54 is mechanically connected to a drain stop 58 in a conventional manner so that the stop can be moved up and down to open and close a drain opening 60 in the bottom 16 of the basin 12 at the foot end 28.

The overflow trough 14 of the preferred embodiment provides approximately 45 gallons of water collection before the water level therein reaches an overflow opening in the bottom of the drain control 54. The overflow is connected via a pipe (not shown) to the waste plumbing of the building. The bottom 48 of the overflow trough 14 is pitched so that water therein runs from the foot end 28 to a suction opening 62 at the head end 26.

In one manner of filling the basin 12 can be filled with water (and bathing oils, soaps or aroma agents) until water spills over the rim 32 and into the overflow trough 14. Once the water within the overflow trough 14 reaches a certain height (described below), a recirculation pump 64 can be activated to draw water in the overflow trough 14 through the suction opening 62. As best appreciated by viewing FIG. 4, the suction opening 62 can be capped by a removable cover 67 having openings for water to pass through and a screen 66 for collecting hair and other particles in the water thereby preventing the debris from entering the recirculation pump 64 and being re-introduced into the basin 12. The screen 66 also can serve to muffle unwanted suction noise. The suction opening 62 leads to a flange 68 mounted beneath the overflow trough 14.

An aerator 70 can be connected to the suction flange 68 via suitable conduit, such as 2 inch PVC piping, at the suction side of the recirculation pump 64. The depicted aerator 70 includes a 6 inch section of 1 inch diameter PVC conduit 74 branching off at a T-coupler 78 vertically upward between the underside of the basin 12 and the overflow trough 14. The throat of the aerator conduit 74 can be closed by a motorized butterfly valve 76 so that the bather has the option of a soak with no effervescence.

The top end of the conduit 74 is covered by a cap 78 having a very small orifice 80, preferably 0.015 inches in diameter. The small orifice 80 allows air to be entrained into the water in the form of tiny bubbles. The bubbles are made even smaller and dispersed by the impeller of the recirculation pump 54 prior to entering the basin 12. Once in the basin, this micro-effervescence clings to the bather's body and rises to the surface slowly and gently.

Referring again to FIGS. 3–5, the recirculation pump 64 is in communication with suction flange 68 and the aerator 70 via the conduit 72. The recirculation pump 64 is preferably a low revolution impeller pump operated by a ⅓ hp motor at approximately 1700 rpm. A preferred recirculation pump of this kind can be obtained from Aquaflow, Inc.

The relatively low speed of this type of pump allows the recirculating pump 64 to run quietly. Thus, the tub can be operated such that there is essentially no pump noise audible above the sound of the spilling water.

The tub 10 also preferably includes a heater 82 for warming the recirculated water before it returns to the basin 12. The heater 82 is connected to the recirculation pump 64 via the conduit 72 and is preferably thermostatically controlled to maintain a water temperature of approximately 103° F. The heater 82 includes a metallic sleeve (not shown) inline with the water conduit in which a heater element (not shown) is disposed. A preferred heater has a 1,500 watt power supply and is commercially available from Hydroquip.

As best shown in FIGS. 1, 6, 12 and 14, water is pumped from the heater 82 through the conduit 72 and reenters the basin 12 through an array of spray nozzles 84, ten of which are disposed in openings roughly ⅓ the way up the basin side walls 18 and 19 and the remaining two being in a vertical wall of the seat 24. The water forced through the nozzles 84 agitates the water in the usual hydrotherapy manner.

Figure 12:
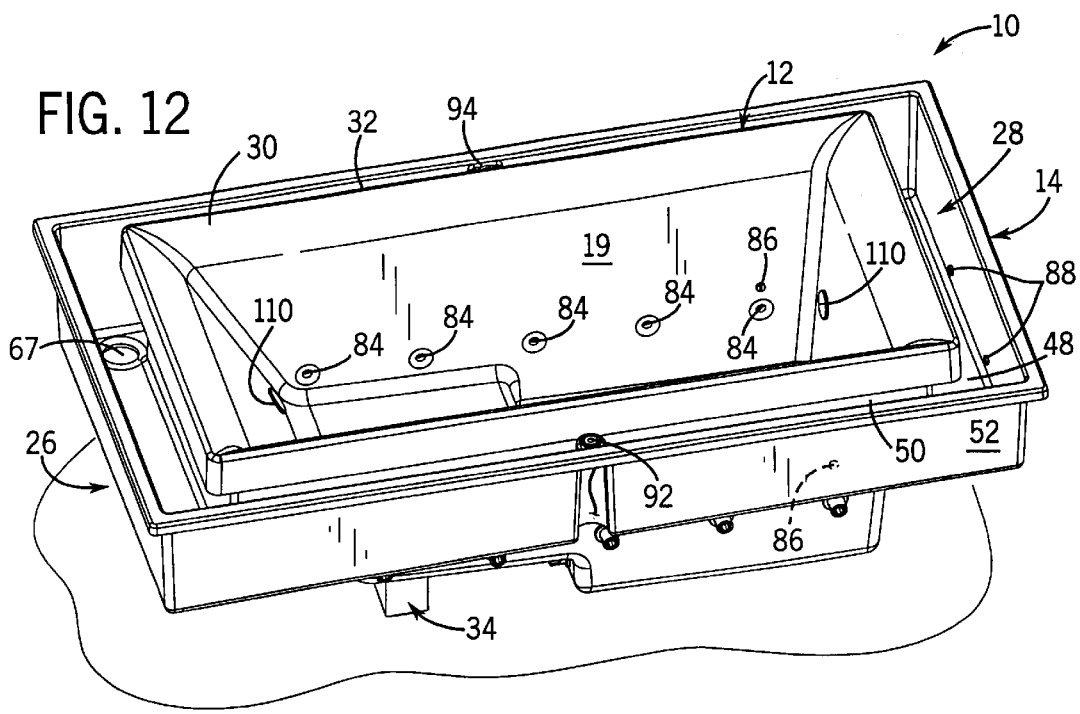
FIG. 12 is another perspective view of the tub of FIG. 1.

Referring to FIG. 12, the tub 10 includes two pair of water level sensors, one pair 86 for each of the basin 12 and the overflow trough 14. The sensors 88 in the overflow trough 14 are spaced apart approximately 8 inches near the bottom 48 at the shallower foot end 28. The sensors 86 in the basin 12 are in opposing side walls 18 and 19 at the foot end 28 slightly above the nozzles 84. Each pair of sensors 86 and 88 have a conductive, metallic face and are electrically coupled to an electronic controller 90 (see FIGS. 3 and 4) in an open circuit.

The sensors 86 and 88 operate by emitting a very low current (on the order of 1 microamp). When water is at or above level of the sensors 86 and 88, then the current is conducted between each pair of sensors to complete the electrical path to the controller. Otherwise, the circuits are open. The sensors are positioned in close proximity to each other to reduce the level of current required to be passed through the water.

The electrical controller 90 has a suitable microprocessing circuitry and is mounted to the underside of the basin 12 next to the recirculation pump 64. The controller 90 is preferably mounted adjacent to the other electronic devices so as to be near a removable access panel in the skirting around the tub 10. The controller 90 receives input signals from the sensors 86 and 88, a power switch 92 and a light switch 94 to control motorized valves, the recirculation pump 64 and a chromatherapy system 96 (described in detail below).

The recirculation pump 64 and aerator 70 are activated by the power switch 92 mounted to the side wall 18 and electrically coupled to the controller 90. The power switch 92 is preferably touch-sensitive and waterproof. Moreover, the power switch 92 can include a ring light 98 that can be illuminated to indicate operation status. Specifically, the ring light 98 flashes green when the water from both the basin 12 and the overflow trough 14 reaches the sensors 86 and 88.

Depressing the power switch 92 will cause a pair of motorized butterfly valves (not shown) in the pump side of the water conduit 72 to open as well as the butterfly valve 76 in the aerator 70. The recirculation pump 64 and aerator 70 will then begin operating and the power switch ring light 98 will illuminate green. This will also activate the chromatherapy system 96 (if not already on) and illuminate a blue ring light 100 of a light switch 94 mounted to the basin side wall 19 and electrically coupled to the controller 90 (as described below).

Depressing the power switch 92 again will turn off the aerator 70 by closing its butterfly valve 76. Depressing the power switch 92 a fourth time will shut off the heater 82 and recirculation pump 64 and close the water conduit butterfly valves. This cycle is repeated by additional activation of the power switch 92.

If the water level is not at the sensors 86 and 88, then the ring light 98 will not be illuminated and the power switch 92 will be inactive. If a bather then depresses the power switch 92 the ring light 98 will flash yellow (rather than green) briefly to provide user feedback and indicate that the system is not ready. If the water level has fallen below either or both pairs of sensors 86 and 88, then the ring lights 98 and 100 will flash and the recirculation pump 64, heater 82 and aerator 70 will be turned off. The chromatherapy system 96 will be turned off only if the water in the basin 12 is below sensors 86.

This auto-off feature prevents the electronic systems from being left activated when no one is bathing, thereby reducing energy costs and the risk of damaging the recirculation pump 64. Note that if the water does fall beneath the sensor depth, the systems can be reactivated by adding water into the basin 12 and depressing the switches 92 and 94 as described.

As mentioned, the tub also includes a chromatherapy system 96 for illuminating the water in the basin 12 to provide soothing visual stimulation for the bather. The chromatherapy system 96 can be one commercially available from Fiberstars of Fremont, Calif. Referring to FIGS. 2 and 9–11, such a chromatherapy system 96 includes a light source 104, a motorized color wheel 106, a fiber optic bundle 108 and four refractive lenses 110. The light source 104, color wheel 106 and an end of the fiber optic bundles 108 are contained in a metal box 112 mounted to the underside of the overflow trough 14 at the head end 26.

The light source 104 is preferably a polychromatic light, such as an incandescent light bulb. The light bulb 104 is positioned to pass light through the color wheel 106 which has seven generally pie-shaped color filters 114 of different hues and an additional unfiltered section 116 so that the water can be illuminated with ordinary, unfiltered light. The color wheel 106 is mounted to a rotatable shaft 118 of a DC motor 120 that can index between each color filter 114 and the unfiltered section 116.

The light bulb 104 is positioned so that it focuses the filtered light to the end of the fiber optic bundle 108. The fiber optic bundle 108 preferably includes 100 fibers that are divided into four 25 fiber cables 122 leading from the metal box 112 to each refractive lens 110, two of which are mounted through the foot wall 20 and two through the back rest 22 of the basin 12. The cables 122 and lenses 110 have suitable mating plug and socket connections facilitating optical coupling as known in the art. The chromatherapy system 96 is activated by the light switch 99, which being suitably controlled by the controller 90, can be used to cycle the color wheel 106 through one or more revolutions, pausing at each color filter 114 and the unfiltered section 116 for slightly less than 10 seconds.

In operation, when a bather depresses the light switch 94, the ring light 100 around the light switch 94 illuminates blue and the light bulb 104 turns on. The water in the basin 12 then becomes illuminated to whatever color was last used. Depressing the light switch 94 a second time will cause the ring light 100 to flash and the motor 120 will be activated to cycle the color wheel 106. The bather can then see the water illuminated to each of the possible colors (including unfiltered light). When the water is illuminated to the desired color, the bather can depress the light switch 94 a third time to deactivate the motor 120 and stop the cycling. Pressing the light switch 94 again turns off the chromatherapy system 96.

In the preferred embodiment the light switch 94 is only operable when the water level is above the sensors 86 in the basin 12. As such, the controller 90 is programmed to automatically shut off the chromatherapy system 96 when the basin 12 is drained below the basin sensors 66. The light switch 94, like the power switch 92, is preferably touch-sensitive and sealed so as to be unaffected by splashing water. The ring light 100 of the light switch 94 will also flash when the water in the basin 12 falls below the sensors 86 and when it is depressed while the chromatherapy system 96 is inactive.

It should be noted that other lighting arrangements could be used without departing from the scope of the present invention. For example, it is possible to replace the fiber optic system entirely with a system of one or a grouping of LEDs in each lens. The grouping of LEDs could include LEDs that illuminate different colors when energized so that the LED colors blend to produce a desired hue. A diffuser filter could be included inside of the lens cover to disperse the light so that individual LEDs cannot be seen separately.

While specific embodiments of the present invention have been described above, various modifications falling within the breadth and scope of the invention will be apparent to one skilled in the art. For example, the basin could be of any other suitable shape, such as round or oval, with a trough of corresponding shape around it. Thus, the following claims should be looked to in order to understand the full scope of the invention.

INDUSTRIAL APPLICABILITY

The above disclosed invention provides a recirculating soaker tub allowing deep water bathing with an aesthetically pleasing continuous overflow.

We claim:
1. A bath tub, comprising:
   a bathing basin having a bottom wall and side walls extending to an upper rim;
   an overflow trough disposed radially outward around at least a majority of a perimeter of the basin for collecting water falling from the upper rim, the overflow trough having a bottom wall spaced below the upper rim of the basin and above the bottom wall of the basin;
   a conduit providing fluid communication between the overflow trough and basin; and
   a pump associated with the conduit for delivering water from the trough to the basin.
2. The bath tub of claim 1, wherein the upper rim of the basin is higher than an uppermost part of the overflow trough.
3. The bath tub of claim 1, wherein the bottom wall of the basin forms a raised seat area.
4. The bath tub of claim 1, wherein the trough surrounds the perimeter of the basin at one height.
5. The bath tub of claim 1, further comprising adjustable leveling feet attached to an underside of the basin.
6. The bath tub of claim 1, wherein the upper rim of the basin extends at one height.
7. The bath tub of claim 1, wherein the basin includes a smoothed surface at the underside of the basin to which the overflow trough is adhered to join the overflow trough to the basin.
8. The bath tub of claim 1, further comprising a chromatherapy system for illuminating water within the basin with colored light.
9. The bath tub of claim 1, wherein an overflow drain opening is disposed in a wall of the trough.
10. The bath tub of claim 1, further comprising a filter in the conduit.
11. The bath tub of claim 1, wherein the pump can be operated at a speed below 2,000 revolutions per minute.
12. The bath tub of claim 1, further comprising an aerator coupled to the conduit.
13. The bath tub of claim 12, wherein the aerator is positioned at a suction side of the pump.
14. The bath tub of claim 12, wherein the aerator can be selectively by-passed.
15. A bath tub, comprising:
   a basin having a bottom wall and side walls extending to an upper rim;
   an overflow trough disposed radially outward around at least a majority of a perimeter of the basin for collecting water falling from the upper rim;
   a conduit providing fluid communication between the overflow trough and basin;
   a pump associated with the conduit for delivering water from the trough to the basin; and
   adjustable leveling feet attached to an underside of the basin, wherein at least one leveling foot comprises:
      a mounting block attached to an underside of the basin and having a clearance opening therein;
      a plate mounted to the mounting block and having a threaded bore there through in registration with the clearance opening of the mounting block; and
      a heel having a base from which extends a threaded rod sized to mate with the threaded bore;
      wherein the heel of the leveling foot can be moved vertically relative to the plate.
16. A bath tub, comprising:
   a basin having a bottom wall and side walls extending to an upper rim;

an overflow trough disposed radially outward around at least a majority of a perimeter of the basin for collecting water falling from the upper rim;

a conduit providing fluid communication between the overflow trough and basin;

a pump associated with the conduit for delivering water from the trough to the basin; and a drain control that operates a drain plug disposed in a drain opening in the bottom wall of the basin, wherein the drain control is mounted to an inner side wall of the overflow trough.

17. The bath tub of claim 16, wherein the drain control is directly below a ledge of the basin so as to be sheltered thereby.

18. A bath tub, comprising:

a basin having a bottom wall and side walls extending to an upper rim;

an overflow trough disposed radially outward around at least a majority of a perimeter of the basin for collecting water falling from the upper rim;

a conduit providing fluid communication between the overflow trough and basin;

a pump associated with the conduit for delivering water from the trough to the basin; and a water level sensing system electrically coupled to the pump such that the pump will not operate if the water level within the basin is below a selected first level or the water level in the overflow trough is below a selected second level.

19. A bath tub, comprising:

a basin having a bottom wall and side walls extending to an upper rim;

an overflow trough disposed radially outward around at least a majority of a perimeter of the basin for collecting water falling from the upper rim;

a conduit providing fluid communication between the overflow trough and basin;

a pump associated with the conduit for delivering water from the trough to the basin; and a chromatherapy system for illuminating water within the basin with colored light, wherein the chromatherapy system is polychromatic and has a spectral filter in the form of a rotatable color wheel.

20. A bath tub, comprising:

a basin having a bottom wall and side walls extending to an upper rim;

an overflow trough disposed radially outward around at least a majority of a perimeter of the basin for collecting water falling from the upper rim;

a conduit providing fluid communication between the overflow trough and basin;

a pump associated with the conduit for delivering water from the trough to the basin; and a chromatherapy system for illuminating water within the basin with colored light, wherein the chromatherapy system will only illuminate the basin when water within the basin electrically couples a pair of basin sensors.

* * * * *